(12) United States Patent
Fladoos

(10) Patent No.: US 10,350,109 B1
(45) Date of Patent: Jul. 16, 2019

(54) FLEXIBLE ADHESIVE PHYSIO TAPE WITH COOLING PROPERTIES

(71) Applicant: Jason Fladoos, Santa Monica, CA (US)

(72) Inventor: Jason Fladoos, Santa Monica, CA (US)

( * ) Notice: Subject to any disclaimer, the term of this patent is extended or adjusted under 35 U.S.C. 154(b) by 0 days.

(21) Appl. No.: 16/120,651

(22) Filed: Sep. 4, 2018

Related U.S. Application Data

(63) Continuation-in-part of application No. 16/022,569, filed on Jun. 28, 2018.

(51) Int. Cl.
| | |
|---|---|
| *A61F 13/00* | (2006.01) |
| *A61F 7/03* | (2006.01) |
| *A61F 7/10* | (2006.01) |
| *A61F 13/02* | (2006.01) |
| *A61F 7/02* | (2006.01) |

(52) U.S. Cl.
CPC .............. *A61F 7/03* (2013.01); *A61F 7/10* (2013.01); *A61F 13/00063* (2013.01); *A61F 13/0243* (2013.01); *A61F 2007/0226* (2013.01); *A61F 2007/0244* (2013.01); *A61F 2007/0276* (2013.01)

(58) Field of Classification Search
USPC ......................................................... 602/1, 2
See application file for complete search history.

(56) References Cited

U.S. PATENT DOCUMENTS

| | | | |
|---|---|---|---|
| 5,431,622 A * | 7/1995 | Pyrozyk .............. | A61F 13/0203 602/2 |
| 9,681,994 B2 * | 6/2017 | Case-Gustafson ......................... | A61F 13/15203 |
| 2006/0002988 A1 * | 1/2006 | Ellefson ............ | A61F 13/00063 424/448 |
| 2006/0282138 A1 * | 12/2006 | Ota .......................... | A61F 7/03 607/96 |
| 2008/0147153 A1 * | 6/2008 | Quincy ..................... | A61F 7/03 607/114 |
| 2010/0234785 A1 * | 9/2010 | Liebowitz ............. | A61F 5/0118 602/61 |
| 2010/0298747 A1 * | 11/2010 | Quinn ....................... | A61F 5/40 602/1 |
| 2013/0060209 A1 * | 3/2013 | Tyler ................. | A61F 13/00063 604/307 |

(Continued)

*Primary Examiner* — Kim M Lewis
(74) *Attorney, Agent, or Firm* — William J. Benman; Benman, Brown & Williams

(57) ABSTRACT

A flexible adhesive kinesiology/physio tape of the present invention adapted adapted to provide thermo-dynamic cooling. In a most general embodiment, the inventive tape includes flexible adhesive kinesiology or physio tape with thermal cooling properties including: a first layer of flexible adhesive high quality porous fabric; a second layer of flexible self-adhesive or skin adhesive high quality porous fabric; and a third layer of flexible endothermic material, sandwiched between the first and second layers. In the illustrative embodiment, the tape is a sheet of high quality porous fabric with a blend of cotton, latex or nylon and the third layer is constructed with reactants effective to cause an endothermic chemical reaction. A breakable barrier separates the reactants so cooling can be initiated at any point by manually breaking the barrier. The third layer can be implemented with liquid, with sealed borders, or with solid reactants that could be saturated or interwoven with reactants.

19 Claims, 1 Drawing Sheet

(56) References Cited

U.S. PATENT DOCUMENTS

| | | | |
|---|---|---|---|
| 2014/0243940 A1* | 8/2014 | Schuller | A61F 7/106 607/110 |
| 2014/0257155 A1* | 9/2014 | Altinok | A61H 39/04 602/1 |
| 2015/0217098 A1* | 8/2015 | Hicken | A61L 15/44 602/1 |
| 2018/0289530 A1* | 10/2018 | van den Dries | A61F 13/02 |

* cited by examiner

FLEXIBLE ADHESIVE PHYSIO TAPE WITH COOLING PROPERTIES

BACKGROUND OF THE INVENTION

Field of the Invention

The present invention relates to tapes and bindings. More specifically, the present invention relates to therapeutic physio and kinesiology tapes and bindings.

Description of the Related Art

Physio tape (aka kinesiology tape) is a tape that is used for treating athletic injuries and a variety of physical disorders. Physio tape is conventionally a thin, stretchy, elastic cotton strip with an acrylic adhesive. Therapeutic physio tape can be used to treat inflammation as well as a wide variety of musculoskeletal and sports injuries. Physio tape may be manufactured to emulate human skin in both thickness and elasticity to allow the tape to be worn without binding, constriction or restriction of movement.

Physio tapes generally provide support. However, therapists are likely to appreciate that there is a need in the art for a tape that provides support as well as thermal properties such as heat or cold.

U.S. Patent Application entitled flexible ADHESIVE PHYSIO TAPE WITH THERMAL PROPERTIES filed Jun. 28, 2018 by J. Fladoos, Ser. No. 16/022,569, the teachings of which are incorporated herein by reference, discloses and claims a physio tape that provides support as well as thermal heating properties.

Accordingly, a need remains in the art for a physio tape that provides support along with thermal cooling properties.

SUMMARY OF THE INVENTION

The need in the art is addressed by the flexible adhesive kinesiology/physio tape of the present invention adapted to provide thermo-dynamic cooling. In a most general embodiment, the inventive tape includes flexible adhesive kinesiology or physio tape with thermal cooling properties including: a first layer of flexible adhesive high quality porous fabric; a second layer of flexible self-adhesive or skin adhesive high quality porous fabric; and a third layer of flexible endothermic material, sandwiched between the first and second layers.

In the illustrative embodiment, the tape is a sheet of high quality porous fabric with a blend of cotton, latex or nylon and the third layer is constructed with reactants effective to cause an endothermic chemical reaction. A breakable barrier separates the reactants so cooling can be initiated at any point by manually breaking the barrier. The third layer can be implemented with liquid, with sealed borders, or with solid reactants that could be saturated or interwoven with reactants.

Hence, in a first embodiment, the reactants are dry solid compounds such as ammonium nitrate, calcium ammonium nitrate, potassium chloride, ammonium chloride or urea and the tape is adapted for activation by breaking a barrier separating water filled chambers and chambers with one or more of the dry compounds, allowing them to mix to initiate the endothermic reaction. Hollow chambers constructed of leak-proof material hold and separate raw reactants enclosed in a flexible leak-proof container that will fit into each chamber. The reactants could include barium hydroxide octahydrate crystals and dry ammonium chloride; thionyl chloride ($SOCl_2$) and cobalt (II) sulfate heptahydrate; ethanoic acid and sodium carbonate or other suitable water activated enthothermic reactants. The tape includes a strong adhesive such as zinc oxide.

In a second dry embodiment, the third layer is implemented as a powder or crystal.

The tape could be constructed with multiple layers of pre-made reactant strips that are stacked or glued onto each other and separated by a barrier breakable by hand. The tape could have segmented lengths of endothermic reactants to allow for the tape to be cut at various lengths without cutting through a layer of reactants.

DESCRIPTION OF THE INVENTION

Illustrative embodiments and exemplary applications will now be described with reference to the accompanying drawings to disclose the advantageous teachings of the present invention.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Figure 1:
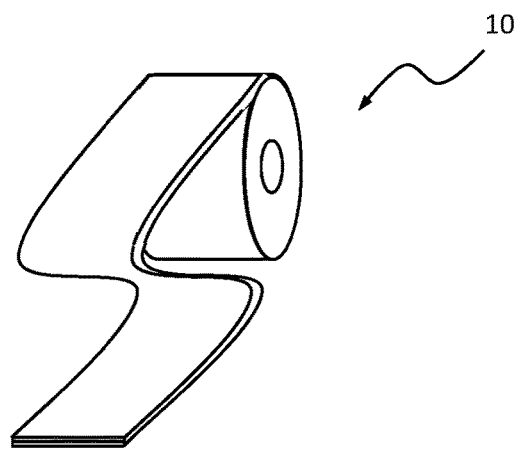
FIG. 1 is a perspective view of a roll of thermal tape implemented in accordance with the teachings of the present invention.

FIG. 1 is a perspective view of a roll of thermal tape implemented in accordance with the teachings of the present invention.

Figure 2:
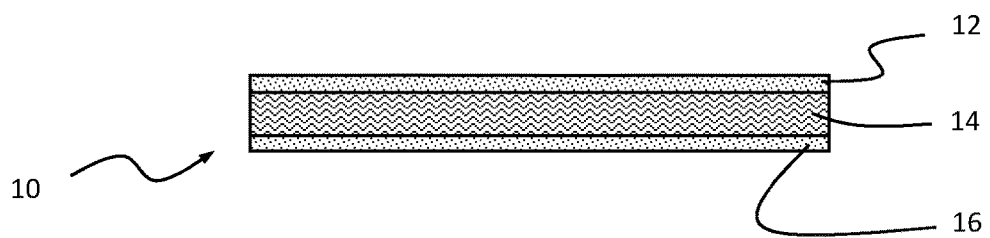
FIG. 2 is a sectional end view of the tape depicted in FIG. 1.

FIG. 2 is a sectional end view of the tape depicted in FIG. 1. As shown in FIGS. 1 and 2, the present invention is flexible adhesive kinesiology/physio tape adapted to produce cold from and endothermic reaction. In the preferred embodiment, the inventive flexible adhesive kinesiology or physio tape 10 with thermal cooling properties includes a first layer 12 of flexible adhesive high quality porous fabric, a second layer 16 of flexible self-adhesive or skin adhesive high quality porous fabric; and a layer 14 of flexible endothermic material, sandwiched between the first and second layers 12 and 16 respectively. The third layer 14 is constructed with reactants effective to cause an endothermic chemical reaction.

In a first embodiment, the reactants are dry, solid compounds such as ammonium nitrate, calcium ammonium nitrate, potassium chloride, ammonium chloride or urea. In this embodiment, the tape is activated by breaking a barrier separating water filled chambers and chambers with one or more of the above-mentioned dry compounds, allowing them to mix initiating an endothermic reaction.

In an alternative embodiment, the endothermic reaction is effectuated with dry compounds using, by way of example:
- the reaction of barium hydroxide octahydrate crystals with dry ammonium chloride;
- the reaction of thionyl chloride ($SOCl_2$) with cobalt (II) sulfate heptahydrate; and/or
- reacting ethanoic acid with sodium carbonate Some of these reactions may not be ideal for the human skin application but could be an option for wrapping the tape around a food or beverage container or any inanimate object with the intention of it being cooled.

Layer 14 can be created as multiple layers saturated or interwoven with the reactants or it can be implemented as a powder/crystal form or liquid with sealed borders.

The inventive tape 10 may be fabricated by applying a strong adhesive such as zinc oxide or other suitable adhesive to a large sheet of high quality porous fabric 16 such as a blend of cotton, latex and/or nylon.

Next, the top layer 12, fabricated in the same manner as the bottom layer 16, is applied to the endothermic layer 14. The top and bottom layers 12 and 16 may be 97% tightly woven elasticated cotton with 3% nylon fibers or implemented with a ratio of cotton or nylon better suited for a particular application.

In an alternative embodiment, a hollow section of the tape 10 could be provided and filled with a pre-made, plastic, enclosed tube of reactants. This eliminates the need for the tape to be leak proof. This also simplifies the manufacturing process as the tape can be made with a hollow core and then tubes can be inserted that are either filled with reactants that cool or heat. Those tubes can also be filled with varying quantities depending on the desired intensity of heat or cool.

Structure of the Cold Tape:

The tape may be constructed in multiple ways. The tape may be constructed to contain hollow chambers that can hold and separate the individual reactants.

In accordance with the present invention, individual reactants can either be enclosed in a flexible, leak-proof container that will fit into each chamber of the tape or the tape can be constructed of leak-proof material so the raw reactants can be placed directly inside each chamber. In either aspect, there will have to be a breakable barrier that separates the reactants, so the cooling can be initiated at any point by breaking the barrier.

The tape could also be constructed with multiple layers of pre-made reactant strips that are stacked or glued onto each other but separated by a barrier. Squeezing the tape by hand could break the barriers and initiate the endothermic reaction.

Practical Uses and Temperature Ranges:

Human use: Tape being adhered to the skin can't be too cold as you want to avoid freezing and/or damaging the skin. Typical cold packs reach 3 degrees Celsius or 37.4 degrees Fahrenheit, but this range can be adjusted to desired temperature by changing the chemical equation and reactant amounts. This adjustment can change the temperature range as well as length of cooling time.

Non-human use: Tape being adhered to an inanimate object can be made as cold as needed depending on the desired outcome. Practical uses are cooling warm beverages or freezing water to produce ice in remote areas. Again, the reactants can be adjusted to obtain the desired temperature and length of cooling time.

Dimensions of the Cold Tape:

In the best mode, the tape has a width of 1-4 inches, a thickness of 1-5 mm and a length of 6 inches to any length. The tape can be manufactured to have segmented lengths of endothermic reactants to allow for the tape to be cut at various lengths without cutting through the container, pouch or layer of reactants.

Those of ordinary skill in the art will appreciate that the present invention is not limited to the fabrics and chemicals disclosed herein. Other combinations of fabrics and chemicals may be employed without departing from the scope of the present teachings. For example, a plurality of small capsules may be provided within the tape which, when squeezed by a user, ruptures and releases a mix of chemicals leading to an endothermic cooling effect.

Those having ordinary skill in the art and access to the present teachings will recognize additional modifications, applications and embodiments within the scope thereof.

It is therefore intended by the appended claims to cover any and all such applications, modifications and embodiments within the scope of the present invention.

The invention claimed is:

1. A flexible adhesive kinesiology or physio tape with thermal cooling properties including:
   a first layer of flexible elastic adhesive high quality porous fabric;
   a second layer of flexible elastic self-adhesive or skin adhesive high quality porous fabric;
   and a third layer of flexible endothermic material, sandwiched between the first and second layers.

2. The flexible adhesive kinesiology or physio tape of claim 1 wherein the third layer is constructed with reactants effective to cause an endothermic chemical reaction.

3. The flexible adhesive kinesiology or physio tape of claim 2 further including a breakable barrier that separates the reactants so the cooling can be initiated at any point by breaking the barrier.

4. The flexible adhesive kinesiology or physio tape of claim 2 wherein the reactants are dry solid compounds such as ammonium nitrate, calcium ammonium nitrate, potassium chloride, ammonium chloride or urea.

5. The flexible adhesive kinesiology or physio tape of claim 4 wherein the tape is adapted for activation by breaking a barrier separating water filled chambers and chambers with one or more of the dry compounds, allowing them to mix to initiate the endothermic reaction.

6. The flexible adhesive kinesiology or physio tape of claim 2 wherein the reactants include barium hydroxide octahydrate crystals and dry ammonium chloride.

7. The flexible adhesive kinesiology or physio tape of claim 2 wherein the reactants include thionyl chloride (SOC12) and cobalt (II) sulfate heptahydrate.

8. The flexible adhesive kinesiology or physio tape of claim 2 wherein the reactants include ethanoic acid and sodium carbonate.

9. The flexible adhesive kinesiology or physio tape of claim 1 wherein the third layer includes multiple layers saturated or interwoven with reactants.

10. The flexible adhesive kinesiology or physio tape of claim 1 wherein the third layer is implemented as a powder or crystal.

11. The flexible adhesive kinesiology or physio tape of claim 1 wherein the third layer is a liquid with sealed borders.

12. The flexible adhesive kinesiology or physio tape of claim 1 wherein the tape is a sheet of high quality porous fabric with a blend of cotton, latex or nylon.

13. The flexible adhesive kinesiology or physio tape of claim 12 wherein the adhesive is zinc oxide.

14. The flexible adhesive kinesiology or physio tape of claim 1 wherein the tape includes hollow chambers that hold and separate the reactants.

15. The flexible adhesive kinesiology or physio tape of claim 14 wherein the individual reactants are enclosed in a flexible leak-proof container that will fit into each chamber.

16. The flexible adhesive kinesiology or physio tape of claim 14 wherein the tape is constructed of leak-proof material.

17. The flexible adhesive kinesiology or physio tape of claim 16 wherein the tape includes raw reactants mounted directly inside each chamber.

18. The flexible adhesive kinesiology or physio tape of claim 1 wherein the tape is constructed with multiple layers of pre-made reactant strips that are stacked or glued onto each other and separated by a barrier breakable by hand.

19. The flexible adhesive kinesiology or physio tape of claim 1 wherein the tape has segmented lengths of endothermic reactants to allow for the tape to be cut at various lengths without cutting through a layer of reactants.

\* \* \* \* \*